United States Patent
Hultqvist et al.

(10) Patent No.: US 10,843,008 B2
(45) Date of Patent: Nov. 24, 2020

(54) SYSTEM AND METHOD FOR ATTAINING TARGET DOSE CONFORMITY IN ION BEAM TREATMENT

(71) Applicant: RaySearch Laboratories AB, Stockholm (SE)

(72) Inventors: Martha Hultqvist, Stockholm (SE); Terese Nordström, Farsta (SE)

(73) Assignee: RaySearch Laboratories AB, Stockholm (SE)

(*) Notice: Subject to any disclaimer, the term of this patent is extended or adjusted under 35 U.S.C. 154(b) by 0 days.

(21) Appl. No.: 16/471,125

(22) PCT Filed: Dec. 20, 2017

(86) PCT No.: PCT/EP2017/083762
§ 371 (c)(1),
(2) Date: Jun. 19, 2019

(87) PCT Pub. No.: WO2018/115094
PCT Pub. Date: Jun. 28, 2018

(65) Prior Publication Data
US 2020/0038682 A1 Feb. 6, 2020

(30) Foreign Application Priority Data
Dec. 22, 2016 (EP) .................................. 16206124

(51) Int. Cl.
*A61N 5/10* (2006.01)
(52) U.S. Cl.
CPC ........... *A61N 5/103* (2013.01); *A61N 5/1077* (2013.01); *A61N 2005/1087* (2013.01)

(58) Field of Classification Search
CPC .................. A61N 5/1077; A61N 5/103; A61N 2005/1087
See application file for complete search history.

(56) References Cited

U.S. PATENT DOCUMENTS

| 2004/0200983 | A1  | 10/2004 | Fujimaki et al. |
| 2016/0082289 | A1* | 3/2016  | Frigo ................... A61N 5/103 600/1 |

FOREIGN PATENT DOCUMENTS

EP    1 763 293 A2    3/2007

OTHER PUBLICATIONS

EP Search Report dated Jun. 7, 2017 for EP16206124.6.

* cited by examiner

*Primary Examiner* — Christine H Matthews
*Assistant Examiner* — Joshua Daryl D Lannu
(74) *Attorney, Agent, or Firm* — Faegre Drinker Biddle & Reath LLP

(57) ABSTRACT

The present disclosure relates to a system, a method, a computer program and a computer readable medium for determining the thickness of a range shifter to attain target dose coverage in ion beam treatment, wherein the range shifter is for use in a machine for radiation treatment of a target volume, by: receiving, in a processor, input parameters comprising a radiation energy parameter, a range shifter material parameter, object geometry information, and beam characteristic parameters; and further calculating, for each of at least one delivery direction, a range shifter thickness, based on the input parameters, which will deliver the optimum dose conformity.

10 Claims, 4 Drawing Sheets

SYSTEM AND METHOD FOR ATTAINING TARGET DOSE CONFORMITY IN ION BEAM TREATMENT

This application is the National Stage of International Application No. PCT/EP2017/083762, filed Dec. 20, 2017, and claims benefit of European Patent Application No. 16206124.6, filed Dec. 22, 2016, the entire contents of which are incorporated by reference herein.

THE BACKGROUND OF THE INVENTION AND PRIOR ART

The present invention relates generally to solutions for attaining target dose coverage in ion beam radiation treatment of a target volume, while minimizing unwanted dose to surrounding tissue. More particularly, the invention relates to a system and a corresponding method for determining range shifter settings in ion beam treatment, such that both target dose coverage and minimized unwanted dose is obtained. The invention also relates to a computer program and a processor-readable medium.

Radiation treatment typically involves subjecting a target, such as a tumour within a patient, to one or more radiation beams. Ideally, a specific radiation dose should be delivered to the target while minimal dose should reach the surrounding tissue and organs. In particular, the dose to critical tissues or organs, such as the heart, bladder or spine, depending on where the tumour is located, should be minimized.

The maximum and minimum doses for various tissues and organs are specified in a set of clinical goals. To verify a calculated radiation dose, the one or more radiation beams may instead be subjected to a phantom.

In the field of radiation therapy treatment planning, both within traditional photon treatment, but also within ion beam treatments, the user creates a radiation treatment plan prior to treatment delivery, herein after also referred to as a treatment plan, after having knowledge of the to-be-treated target volume in a patient's body, in a phantom or the like, for example by using a computer tomography (CT) scanner. If the target volume is comprised in a patient, the target volume is usually an organ or part of an organ in the patient's body that is affected by a tumour, for example a cancer.

The use of inadequate treatment planning methods often leads to inadequate radiation therapy treatment plans, which in turn leads to poor target dose coverage and/or unwanted dose distribution reaching the surrounding tissue and organs. In worst case, this may lead to the target volume not receiving the required treatment dose and/or damage to critical tissues or organs.

In active techniques, the ions are delivered by modulated pencil beams within a certain range of treatment energies, which are supported by the radiation treatment machine. The energy of the pencil beam will determine the ion range in the beam direction. To reach a desired depth, the ion range can be adjusted by using range shifters of water-equivalent materials, placed between the radiation treatment machine and the patient or phantom, which will decrease the ion range in the patient or phantom.

Range shifters are used to adjust the ion range in order to reach the depths where the target is located, that is to achieve target depth coverage, herein after also referred to as target coverage. Range shifters are needed when the machine's lower energy limit is too high to cover shallow targets, to overcome the problem of not being able to deliver radiation to superficial targets. Range shifters are also used with machines that support a fixed number of energies, and where the intervals between the fixed energies are large. In this case, range shifters are used to cover the depth intervals where target coverage would otherwise be difficult to achieve.

The inventors have found that there is still a need for novel methods and strategies that allow improving upon or optimizing existing parameter generation and/or radiation treatment plans, to minimize dose to healthy tissue, i.e. to achieve improved target dose conformity, while maintaining target coverage.

SUMMARY OF THE INVENTION

The object of the present invention is therefore to offer a solution for improving or optimizing upon existing parameter generation for radiation treatment plans, to achieve improved target dose conformity while maintaining target coverage. The object is obtained by providing a method for calculating and presenting an optimum thickness of a range shifter in ion beam scanning that delivers the desired dose distribution, achieving improved target dose conformity while maintaining target coverage, for different machine energy settings.

The target dose conformity is affected by the lateral dose fall-off (penumbra) and is improved with sharper penumbra, hereinafter also referred to as better/sharper lateral penumbra.

The inventors have realized that since the penumbra of pencil beams is broadened when transported through material, but higher energy pencil beams generally have sharper penumbras than lower energy pencil beams, a combination of high energy with a range shifter, or with a range shifter of higher thickness, might give better/sharper penumbra than a combination of low energy with no, or a thinner, range shifter. Therefore, determining the optimal range shifter thickness is not trivial.

According to one aspect of the invention, the object is achieved by a system for determining a thickness of a range shifter to attain target coverage in ion beam treatment, wherein the range shifter is for use in a machine for radiation treatment of a target volume, the system comprising: a data processor; and a memory, said memory containing instructions executable by said data processor; wherein the data processor is configured to: receive input parameters, comprising: a radiation energy parameter; a range shifter material parameter; object geometry information; and beam characteristic parameters; wherein the data processor is further configured to calculate, for each of at least one delivery direction, a range shifter thickness, based on the input parameters, which will deliver the optimum dose distribution, achieving improved target dose conformity while maintaining target coverage.

This system is advantageous because it provides a fast, inexpensive and accurate basis for decision on system settings, including range shifter selection/range shifter settings, for each radiation beam delivered by a treatment planning machine.

This in turn gives an improved basis for generating a treatment plan leading to optimized radiation treatment with regard to sharp penumbra in combination with improved, or maintained, target coverage.

The sharper penumbra in combination with improved, or maintained, target coverage, gives an improved dose distribution. In other words, the risk of under dosage of the target and/or over dosage of healthy tissue that may lead to side effects for the patient is reduced.

According to one embodiment of this aspect of the invention, the data processor is further configured to determine a radiation treatment plan for a treatment volume associated with at least one target and in many cases at least one organ-at-risk, using, for each of the at least one delivery direction, the corresponding calculated range shifter thickness.

According to another aspect of the invention, the object is achieved by a method for determining the thickness of a range shifter to attain target dose coverage in ion beam treatment, wherein the range shifter is for use in a machine for radiation treatment of a target volume, the method comprising: receiving, in a processor, input parameters comprising: a radiation energy parameter; a range shifter material parameter; object geometry information; beam characteristic parameters; wherein the method further comprises calculating, for each of at least one delivery direction, a range shifter thickness, based on the input parameters, which will deliver the optimum dose conformity.

According to one embodiment of this aspect of the invention, the method further comprises determining a radiation treatment plan for a treatment volume associated with at least one target and in many cases at least one organ-at-risk, based on, for each of the at least one delivery direction, the corresponding range shifter thickness calculated using the method.

The advantages of the embodiments of the disclosed method are apparent from the discussion above with reference to the proposed system.

According to a further aspect of the invention the object is achieved by a computer program loadable into the memory of at least one processor, and includes software adapted to implement the method proposed above when said program is run on at least one processor.

According to another aspect of the invention the object is achieved by a processor-readable medium, having a program recorded thereon, where the program is to control at least one processor to perform the method proposed above when the program is loaded into the at least one processor.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

Figure 1:
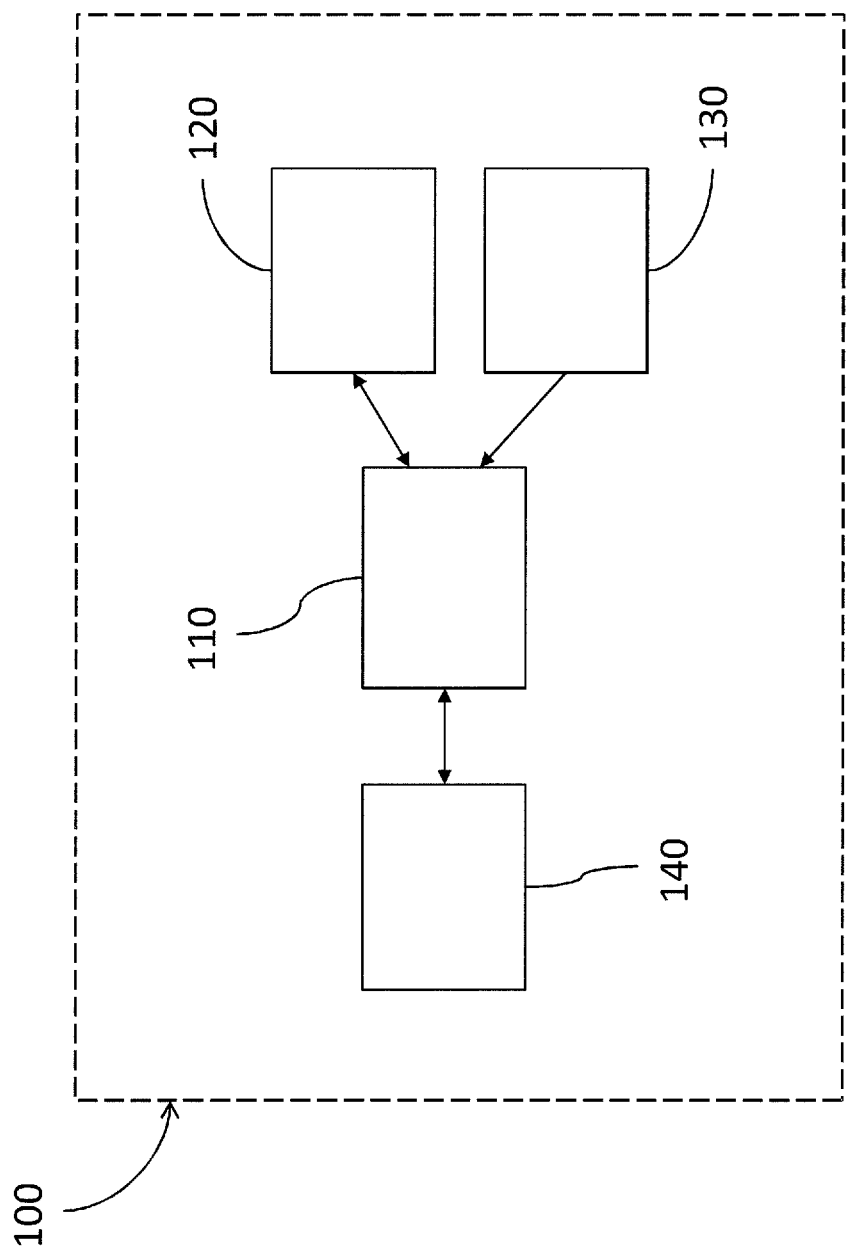
FIG. 1 shows an overview of a system according to one embodiment of the invention.

DESCRIPTION OF PREFERRED
EMBODIMENTS OF THE INVENTION

The inventors have found that there is a need for improving or optimizing upon existing parameter generation for radiation treatment plans, to achieve better target dose conformity while maintaining target coverage.

The aim of the embodiments presented herein is to achieve, when used in a machine for radiation treatment of a target volume, the sharpest possible penumbras at a given radiological depth, while maximizing, or maintaining, target coverage, thereby achieving improved or optimized parameter generation for radiation treatment plan generation.

Ion beam treatment, to which this invention is applicable, can be divided into passive and active techniques. In passive techniques, a broad field of radiation is applied and physical elements are used to shape the beam to match the target as precisely as possible. The invention is applicable for passive techniques; however the main usage will be within active techniques.

In ion beam therapy today, the user cannot retrieve information about the optimum thickness of the range shifter that delivers the sharpest penumbras for different machine energy settings. Instead the clinics have a standard set of range shifters, with fixed thicknesses, which are selected for use based on experience, and which in many cases will not deliver the optimum target dose conformity. Range shifters are typically selected conservatively, e.g. in some cases by favouring a thicker range shifter over a thinner one, but there is no way, using the experience based manual approach, to determine whether the selection does in fact provide the sharpest possible penumbra.

This aim is achieved by systems, methods and computer program products presented herein for determining an optimal range shifter thickness with respect to target dose conformity.

The optimal range shifter thickness is dependent on the radiation treatment machine energy limits, as this is a machine specific parameter. The optimal range shifter thickness is further beam specific and therefore also dependent on characteristics of the output beam. Furthermore, the optimal range shifter thickness with respect to sharp penumbras may be different for different evaluated depths, e.g. the range shifter thickness that is optimal at the most proximal point of the target volume may not be the same as the range shifter thickness that is optimal at the most distal point of the target volume.

For all embodiments presented herein, the result is an optimal range shifter thickness. If the clinic does not have a range shifter of exactly this thickness for immediate use, they could either use the best available thickness, or manufacture one according to the specification.

According to one or more embodiments, the method presented herein is applied to, and the system presented herein, is configured to operate with ion beams in general, which means that it is equally applicable for situations where the beam is divided into two or more sub-beams.

In previous solutions, selection of range shifter/range shifter thickness is done manually, typically based on experience, rough estimations and/or trial and error approach with iterative testing to achieve target coverage. Often, this leads to suboptimal selections of range shifter thickness, or combinations of energy level and range shifter thickness, which in turn gives suboptimal dose conformity.

The methods described herein, and performed by the systems and computer programs according to different aspects and embodiments described herein, are all computerized and performed automatically by means of one or more data processors. The inventive methods would not be practically possible to perform manually, as the calculations involved are extremely complex. A person trying to perform the necessary calculations would have to manually trace each pencil beam through each voxel, taking densities etc. into account. The entire calculation needed for a treatment plan, leading up to decisions about range shifter selection, would take days, or more, since the person calculating, e.g. the treatment planner, would have to take into account a large number of combinations of radiation energy levels, range shifter parameters and a complex object geometry. Of course, days or more for treatment planning is too time consuming and expensive to be an alternative. The automatic calculation according to all embodiments presented herein performs this in a matter of seconds, thereby providing a fast, inexpensive and accurate basis for decisions on machine settings, including range shifter selection/range shifter settings for each radiation beam delivered by a radiation treatment machine. In other words, all embodiments presented herein provide an improved basis for parameter generation and/or generation of radiation treatment plans, leading to optimized radiation treatment with regard to sharper penumbra in combination with improved, or maintained, target coverage.

The solution according to embodiments presented herein further has the advantage of achieving an improved dose distribution, in other words to reduce the risk of under dosage of the target and/or over dosage of healthy tissue that may lead to side effects for the patient.

FIG. 1 shows an overview of a system 100 for determining the thickness of a range shifter in ion beam treatment to attain target dose coverage according to one embodiment of the invention. The system 100 includes a data processor 110 and a memory 140, said memory containing instructions executable by said data processor 110. In other words, the memory 140 is configured to store software for executing the below-described procedure when the software is being run on the processor 110. The system 100 may further comprise a first and second interface, 120 and 130, respectively. For presentation purposes, FIG. 1 illustrates the interfaces 120 and 130 as separate entities. However, in a practical implementation, two or more of the interfaces may be integrated into a common unit.

As described earlier, the ion beam treatment technique used may be an active or a passive technique. One non-limiting example of an active technique, for which the systems and methods presented herein may advantageously be used, is pencil beam scanning.

The first interface 120 is configured to output image data for presentation on a graphical display. In some embodiments, the first interface 120 is configured to output graphical data corresponding to a graphical user interface (GUI) on a graphical display. The GUI may present information and selectable options by which a treatment planner can provide input to the system and methods described herein for calculating one or more optimal range shifter thickness, and optionally also generate a treatment plan using the one or more calculated range shifter thicknesses. The image data is output in response to control instructions from the processor 110.

The data processor 110 is configured to receive input parameters, comprising a radiation energy parameter, a range shifter material parameter, object geometry information, and beam characteristic parameters.

In some embodiments, the memory 140 is configured to store a knowledge database, or predetermined input parameters. The memory 140 may further be configured to send input parameters from the stored knowledge database, or the stored predetermined input parameters, to the data processor 110, possibly in response to a control signal from the data processor 110. Correspondingly, the data processor 110 is in these embodiments configured to send a control signal and/or to receive input parameters from the memory 140.

In some embodiments, the second interface 130 is configured to forward input parameters to the data processor 110. The data processor 110 is in these embodiments configured to receive input parameters from the second interface 130. The input parameters are in these embodiments preferably generated in response to user commands entered via an input device, for example a keyboard and/or computer mouse or other pointing device, touchscreen or any other suitable input device. The input may be provided via a GUI presented on a display by the first interface 120.

According to one or more embodiment, the energy parameter 201 is indicative of one or more radiation energy levels supported by the machine for radiation treatment. In some embodiments, the energy parameter 201 is indicative of a continuous energy level interval, or range of treatment energies, having a minimum energy level and a maximum energy level, which the radiation treatment machine is able to deliver. Of course, the minimum energy level and the maximum energy level that the machine supports corresponds to a minimum and maximum radiological depth, respectively, which the beams delivered by the machine can reach inside the target.

According to one or more embodiment, the range shifter material parameter 203 is indicative of a material density and an elemental composition of a range shifter.

According to one or more embodiment, the object geometry information 205 describes geometric relationships of a part of a patient (human or animal) comprising the target volume. In these embodiments, the target volume is a tumour.

According to another embodiment, the object geometry information 205 describes geometric relationships of a part of a phantom comprising the target volume. This may for example be the case in quality assessment of a treatment radiation dose.

According to one or more embodiment, the object may be a patient, a phantom or other, and the object geometry information 205 comprises image data and information on respective densities of one or more regions in the image data, whereby the data processor 110 may be configured to process image data and information on densities of one or more regions in the image. The image data may be computer tomography (CT) data, but may also be magnetic resonance (MR) data, synthetic CT data, or image data from another source, comprising information on geometry of the target object, i.e. the object that is to be irradiated.

According to one or more embodiment, the beam characteristic parameter 207 comprises a beam angle of incidence and spatial-angular distribution moments of the pencil beams at the isocenter plane. The spatial-angular distribution moments are energy dependent and describe the pencil beam's radial and angular spread at isocenter, and the covariance between them. The evolution of spatial-angular distribution moments when transporting the pencil beam through the range shifter and patient geometry determines the lateral penumbra of the pencil beam and thus influences the target dose conformity.

The data processor 110 is in one or more embodiment further configured to calculate, for each of at least one delivery direction, a range shifter thickness, based on the input parameters, which will deliver the optimum dose conformity.

As previously mentioned, the result of calculating a range shifter thickness based on the input parameters 201, 203, 205, 207, according to embodiments described herein, is an optimal range shifter thickness which will deliver the optimum dose conformity, while maintaining target coverage The system, and corresponding method, embodiments presented herein thereby provide a fast, inexpensive and accurate basis for decision on system settings, including range shifter selection/range shifter settings, for each radiation beam delivered by an ion beam treatment machine. In other words, embodiments presented herein provide an improved basis for generating a treatment plan, thereby improving or optimizing upon existing parameter generation and/or radiation treatment plans. In some embodiments, the data processor 110 is further configured to determine a radiation treatment plan for a treatment volume associated with at least one target and at least one organ-at-risk, using the at least one calculated range shifter thickness. Using the at least one calculated range shifter thickness may include to select a range shifter having the calculated thickness, if such a range shifter is available, to select not to use a range shifter, if this is the most appropriate choice, or select a range shifter that best corresponds to the calculated optimal range shifter thickness, possibly favouring thinner range shifter, since ion beams are broadened when transported through the range shifter and the lateral dose penumbra is thus worsened.

The best, or most appropriate, selection option is therefore in this context the option that provides the best/sharpest possible penumbra, while improving or maintaining target coverage, when used in a radiation treatment machine.

The invention will now be described with reference to the flow diagrams in FIGS. 2 and 3.

Figure 2:
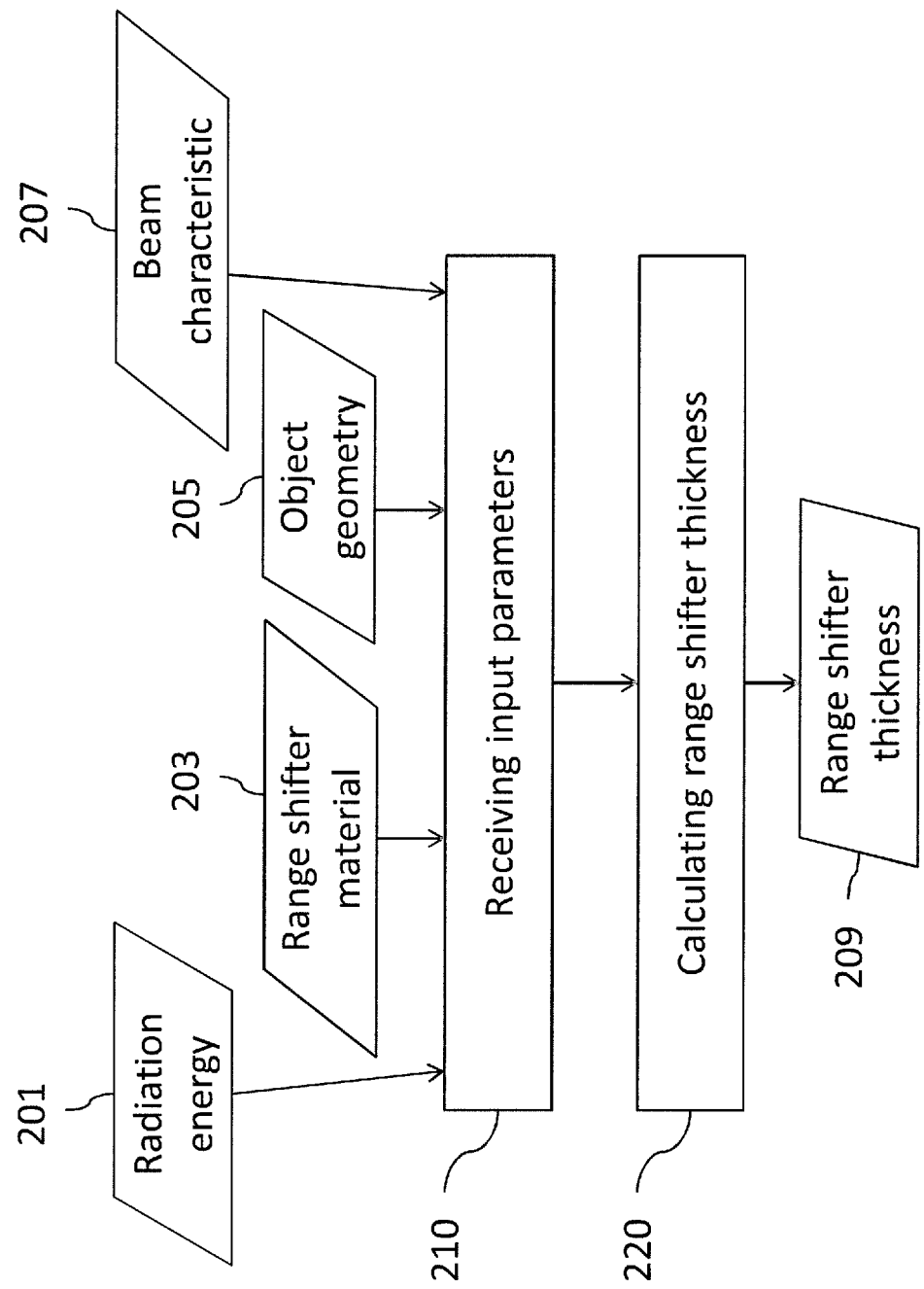
FIG. 2 shows a flow diagram illustrating one embodiment of the proposed method.

FIG. 2 shows a flow diagram of a method, according to one embodiment of the invention In step 210: receiving, in a processor, input parameters comprising: a radiation energy parameter 201; a range shifter material parameter 203; object geometry information 205; and beam characteristic parameters 207.

According to one or more embodiment, the energy parameter 201 is indicative of the energy limits that the machine for radiation treatment is able to deliver, or, if the machine supports fixed discrete energies, one or more radiation energy levels that the machine for radiation treatment is able to deliver.

According to one or more embodiment, the range shifter material parameter 203 is indicative of a material density and an elemental composition of a range shifter.

According to one or more embodiment, the object geometry information 205 describes geometric relationships of a part of a patient comprising the target volume. In these one or more embodiments, the radiation treatment is radiation therapy, and the target volume may for example be a tumour.

According to another embodiment, the object geometry information 205 describes geometric relationships of a part of a phantom comprising the target volume.

According to one or more embodiment, the object geometry information 205 comprises image data and information on respective densities of one or more regions in the image data.

As previously mentioned, the image data may be CT data, but may also be magnetic resonance (MR) data, synthetic CT data, or image data from another source, comprising information on geometry of the target object, i.e. the object that is to be irradiated.

According to one or more embodiment, the beam characteristic parameter 207 comprises a beam angle of incidence and spatial-angular distribution moments of the pencil beams at the isocenter plane. The spatial-angular distribution moments are energy dependent and describe the pencil beam's radial and angular spread at isocenter, and the covariance between them. The evolution of spatial-angular distribution moments when transporting the pencil beam through the range shifter and patient geometry determines the lateral penumbra of the pencil beam and thus influences the target dose conformity.

In step 220: calculating, for each of at least one delivery direction, a range shifter thickness 209, based on the input parameters, which will deliver the optimum dose conformity.

In one or more embodiments, the methods presented herein further comprise selecting the most appropriate range shifter, based on the calculated optimal range shifter and/or the data processor 110 is further configured to select the most appropriate range shifter, based on the calculated optimal range shifter, by, for each of at least one beam direction: calculating, for each available energy, an associated water equivalent thickness needed to cover the target; and determining, from all combinations of available energies and associated water equivalent thicknesses, a combination that provides the sharpest possible penumbra. An optimal range shifter made of water equivalent material would have this thickness. The thickness of an optimal range shifter made of a non-water equivalent material can be calculated based on the water equivalent thickness, in manners known in the art. However, a range shifter of the optimal thickness might, as mentioned herein, not be available at the clinic. The optimal range shifter will thus be compared to the available range shifters in the radiation treatment machine and the closest match will be selected, favouring a range shifter that provides a better target dose conformity over one that provides a worse target dose conformity. The result of the automatic selection can also be that no range shifter should be used. This has the advantage of preventing unnecessary use of range shifters, which is desirable since not using a range shifter gives better lateral penumbras than when using a range shifter.

The optimal range shifter can further be presented to the user, via the GUI, and be used as guidance for future purchases of range shifters. In one or more of these embodiments, the method of any embodiment presented herein further comprises, and/or first interface 120 is further configured to, output graphical data indicative of the optimal range shifter on a graphical display, e.g. via the GUI, thereby presenting the optimal range shifter, or optimal range shifter thickness, to a user.

In some embodiments, a calculated optimal range shifter thickness can be used for evaluation purposes. For example, a treatment plan using the calculated optimal range shifter thickness can be created and compared to a deliverable treatment plan that uses a range shifter that exists at the clinic. The impact on plan quality of using the optimal range shifter thickness can thus be assessed and provide guidance to improvements in range shifter usage.

According to some embodiments, for each beam in a treatment plan to be generated, the user/treatment planner is further enabled to specify whether a range shifter should be automatically selected by the data processor 110. In some embodiments, the first interface 120 is configured to output, in a GUI, one or more selectable options by which a treatment planner can provide input to the system and methods described herein on whether a range shifter should be automatically selected by the data processor 110. The second interface 130 may in turn be configured to forward input parameters indicating a user input selection on whether a range shifter should be automatically selected by the data processor 110 to the data processor 110. The data processor 110 is in these embodiments configured to receive input parameters from the second interface 130. The data processor is in these embodiments further configured to, if the input parameters indicate that the user has selected that a range shifter should be automatically selected by the data processor 110, select a range shifter based on the calculated optimal range shifter. As mentioned herein, the input parameters are in these embodiments preferably generated in response to user commands entered via an input device, for example a keyboard and/or computer mouse or other pointing device, touchscreen or any other suitable input device. The input may be provided via a GUI presented on a display by the first interface 120.

Correspondingly, in some embodiments, the method according to any embodiment presented herein may further comprise: outputting, in a GUI, one or more selectable options by which a treatment planner can provide input to the system and methods described herein on whether a range shifter should be automatically selected; receiving input parameters indicating a user input selection on whether a range shifter should be automatically selected; and, if the input parameters indicate that a range shifter should be automatically selected, selecting a range shifter based on the calculated optimal range shifter.

It is generally advantageous if the processor 110 is configured to effect the above-mentioned procedure by executing a computer program. The processor 110 is therefore preferably communicatively connected to a memory unit storing a computer program product, which, in turn, contains instructions executable by the processor 110; whereby the processor 110 is operative to execute the above-described actions when the computer program product is run on the processor 110.

The range shifter thickness 209 is calculated such that, in combination with the input parameters, it provides the optimal, or best possible, target dose conformity when used in the system for ion beam radiation treatment.

Figure 3:
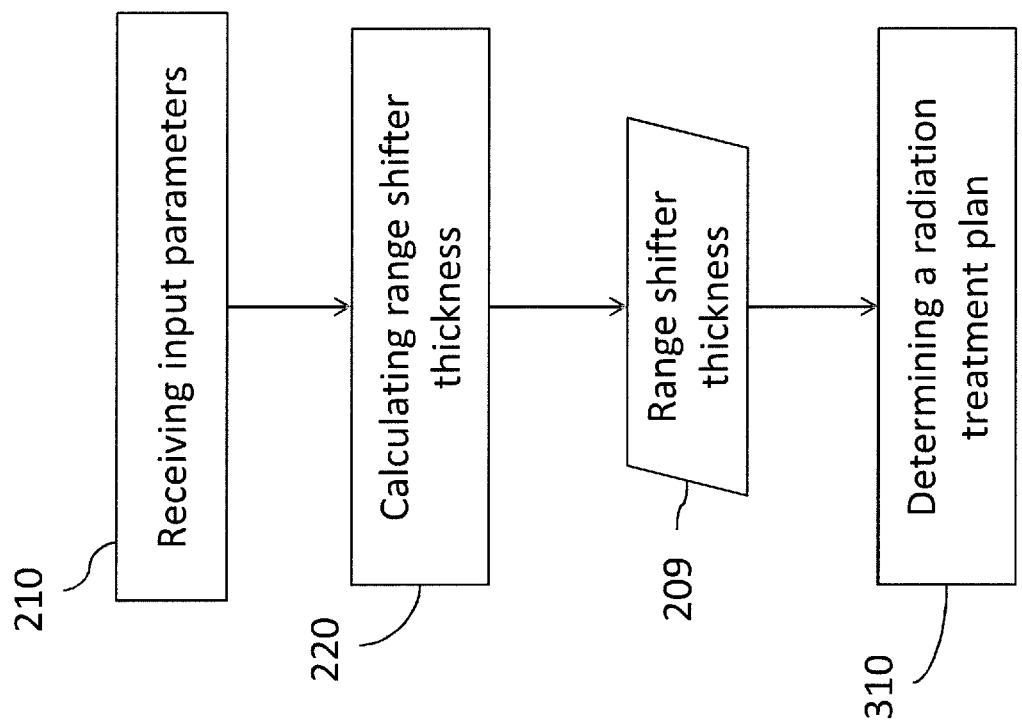
FIG. 3 shows a flow diagram illustrating embodiments of the proposed method.

According to a further aspect, shown in FIG. 3, there is provided a method according to any of the method embodiments presented in connection with FIG. 2, further comprising:

In step 310: determining a radiation treatment plan for a treatment volume associated with at least one target and at least one organ-at-risk, based on at least one range shifter thickness 209 calculated using any of the method embodiments presented herein.

The range shifter thickness 209 is, in one or more embodiment, a function of the radiation energy $E_p$ (energy levels supported by the machine), range shifter material $RS_p$ (density and elemental composition), object geometry $O_{geo}$ and the beam characteristics $B_p$ (angle of incidence and spatial-angular distribution of pencil beam), as shown in equation 1.

$$RS\_thickness = f(E_p, RS_p, O_{geo}, B_p) \quad \text{(Eq. 1)}$$

Parameters that determine the best achievable dose distribution include target coverage (the target must be reached by the ions, including an eventual range shifter) and the lateral dose fall-off (penumbra) which in turn depends on the pencil beam widths. A penumbra that is sharp is in most cases desirable and the size of the penumbra should therefore be minimized.

When calculating the range shifter thickness, which is performed in step 220, the evaluation of pencil beam widths in the Bragg peak, i.e. where the dose delivered by the pencil beam is at its maximum, is performed. The location within the target volume in which the pencil beam widths are evaluated can for instance be at a specific radiological depth of interest, the maximum radiological depth of the target, or as an average over the whole target etc. The location or depth for evaluation may be set in response to user input.

In any of the method embodiments described herein, calculation of a range shifter thickness is a nonlinear optimization problem with a continuous objective function and feasible set. Multiple standard algorithms exist for this class of problems, such as interior-point and sequential quadratic programming methods. It is also computationally feasible to, approximately, solve optimization of a single range shifter thickness by exhaustive enumeration applied to a fine discretization of the feasible set, because this set is one dimensional. For the case when the pencil beam widths shall be minimized at a specific radiological depth of interest, the latter method may for example be performed according to one or more embodiment described in connection with FIG. 4 below.

Figure 4:
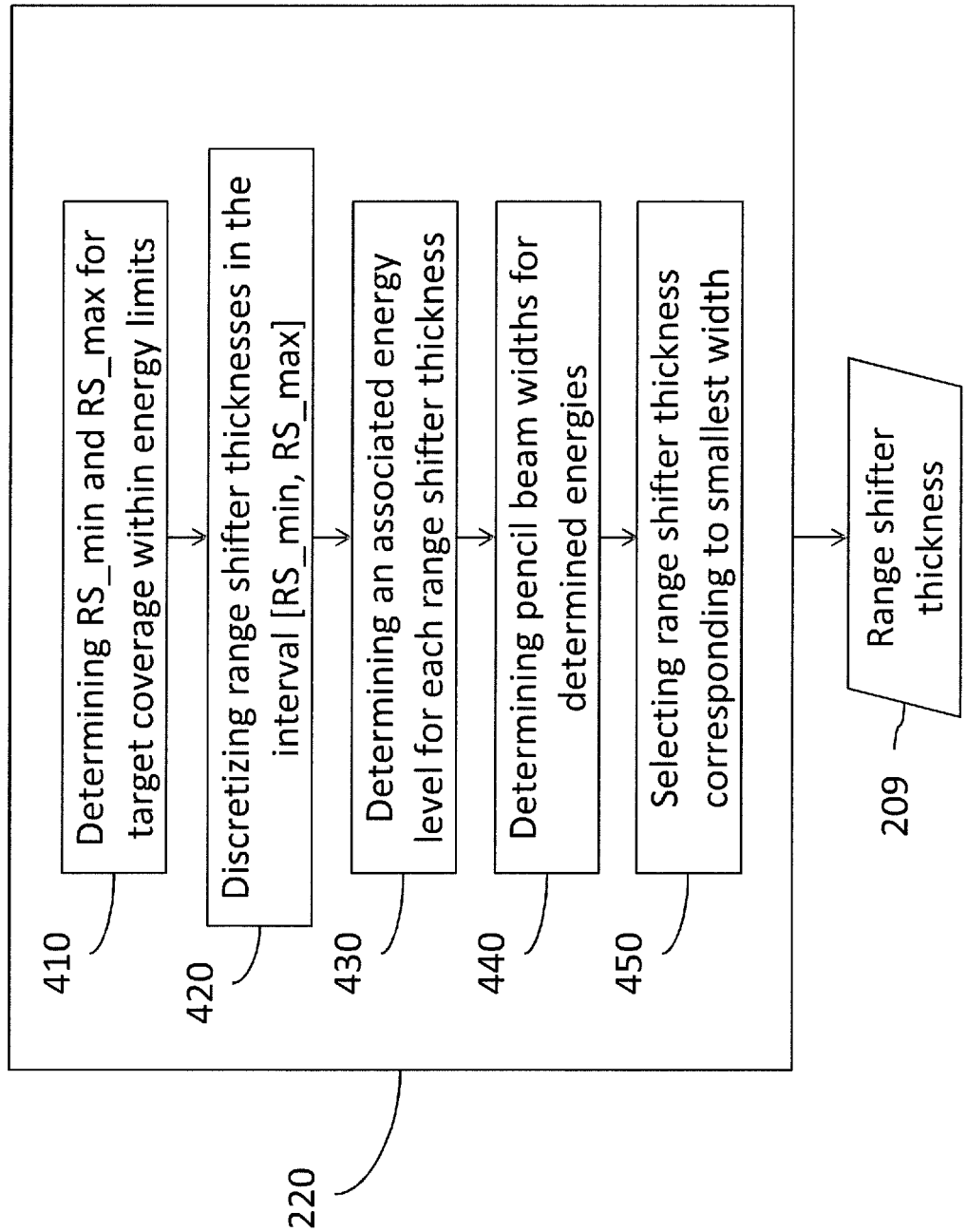
FIG. 4 shows a flow diagram illustrating embodiments of a method for calculating an optimal range shifter thickness.

FIG. 4 shows a flow diagram illustrating embodiments of a method for calculating an optimal range shifter thickness, for which the following input, precondition and relationships are defined:

Input: min_raddepth and max_raddepth, wherein:
    min_raddepth=minimum radiological depth, in other words minimum water equivalent depth of the target; and
    max_raddepth=maximum radiological depth, in other words maximum water equivalent depth of the target Precondition: max_raddepth<R_max, wherein:
    R_max=the range in water of the ions with energy E_max; and
    E_max=the maximum energy limit of the machine.

Relationships:
    E_min=the minimum energy limit of the machine;
    R_min=the range in water of the ions with energy E_min;
    RS_min=lower range shifter thickness limit; and
    RS_max=upper range shifter thickness limit.

In one or more embodiments of the method shown in FIG. 4, the method step 220 of calculating, for each of at least one delivery direction, a range shifter thickness, based on the input parameters, which will deliver the optimum dose conformity, further comprises:

In sub-step 410: determining RS_min and RS_max for target coverage within ion range limits (R_min, R_max).

Determining RS_min and RS_max for target coverage within ion range limits (R_min, R_max) may comprise:
    if R_min>min_raddepth→
        setting RS_min=(R_min−min_raddepth)
    if R_min≤min_raddepth→
        setting RS_min=0;
    and
        setting RS_max=R_max−min_raddepth;

In sub-step 420: discretizing the range shifter thicknesses in the interval [RS_min, RS_max] according to a predetermined step size.

For machines that support discrete energies, sub-step 420 may further comprise determining a subset of the discretized range shifter thicknesses by removing the thicknesses that cannot be combined with the machine's discrete energies to achieve a distal target match.

The method of FIG. 4 further comprises, for each of the discretized range shifter thicknesses, or for each range shifter thickness in the subset in of the discretized range shifter thicknesses if such a subset has been determined:

In sub-step 430: determining an associated energy level to reach the radiological depth of interest.

In step 440: determining the pencil beam width in the Bragg peak for the determined energy of sub-step 430 after transport through the range shifter thickness and patient geometry.

As previously mentioned herein, these calculations are not possible to do by hand, as this would be much too complex and time-consuming, involving the use of CT data (densities+material+beam phase space parameters), or the like, to calculate pencil beam widths at given radiological depths.

The method of FIG. 4 further comprises:

In sub-step 450: comparing the determined pencil beam widths, for all range shifter thicknesses used in sub-steps 430 and 440, to find the smallest width, and selecting as range shifter thickness 209 the range shifter thickness corresponding to the smallest width.

Range shifter thickness 209 is thereby optimized with regard to the present conditions, to provide the optimal, or best possible, target dose conformity when used in the system for ion beam radiation treatment.

The data processor 110 may further be configured to perform calculation of a range shifter thickness using any of the method embodiments described above.

FURTHER EMBODIMENTS

All of the process steps, as well as any sub-sequence of steps, described with reference to FIGS. 2, 3 and 4 above may be controlled by means of a programmed processor. Moreover, although the embodiments of the invention described above with reference to the drawings comprise processor and processes performed in at least one processor, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A system for determining a thickness of a range shifter to attain target dose coverage in ion beam treatment, wherein the range shifter is for use in a machine for radiation treatment of a target volume, the system comprising:
   a data processor; and
   a memory, said memory containing instructions executable by said data processor;
   wherein the data processor is configured to:
      receive input parameters, comprising:
         a radiation energy parameter;
         a range shifter material parameter;
         beam characteristic parameters; and
         object geometry information comprising image data and information on respective densities of one or more regions in the image data;
      calculate, for each of at least one delivery direction, a range shifter thickness, based on the input parameters, which will deliver an optimum dose conformity; and
      create a radiation treatment plan for a treatment volume associated with at least one target and at least one organ-at-risk, using, for each of the at least one delivery direction, the calculated range shifter thickness.

2. The system of claim 1, wherein the energy parameter is indicative of one or more radiation energy levels that the machine for radiation treatment is able to deliver.

3. The system of claim 1, wherein the range shifter material parameter is indicative of a material density and an elemental composition.

4. The system of claim 1, wherein the object geometry information describes geometric relationships of a part of a patient comprising the target volume.

5. A method for determining a thickness of a range shifter to attain target dose coverage in ion beam treatment, wherein the range shifter is for use in a machine for radiation treatment of a target volume, the method comprising:
   receiving, in a processor, input parameters comprising:
      a radiation energy parameter;
      a range shifter material parameter;
      beam characteristic parameters; and
      object geometry information comprising image data and information on respective densities of one or more regions in the image data;
   calculating, for each of at least one delivery direction, a range shifter thickness, based on the input parameters, which will deliver an optimum dose conformity; and
   creating a radiation treatment plan for a treatment volume associated with at least one target and at least one organ-at-risk, based on at least one calculated range shifter thickness.

6. The method of claim 5, wherein the energy parameter is indicative of one or more radiation energy levels that the machine for radiation treatment is able to deliver.

7. The method of claim 5, wherein the range shifter material parameter is indicative of a material density and an elemental composition.

8. The method of claim 5, wherein the object geometry information describes geometric relationships of a part of a patient comprising the target volume.

9. The method of claim 5, wherein the beam characteristic parameters are indicative of a beam angle of incidence and spatial-angular distribution moments of a pencil beam at an isocenter plane.

10. A non-transitory computer readable medium, having a program recorded thereon, where the program is to make at least one processor execute the method according to claim 5 when the program is loaded into the at least one processor.

* * * * *